United States Patent
Jain et al.

(10) Patent No.: US 12,156,877 B1
(45) Date of Patent: Dec. 3, 2024

(54) METHODS OF TREATING CONDITIONS RELATED TO A THIAMINE DEFICIENCY, A THIAMINE-DEPENDENT ENZYME, OR AN ASSOCIATED COFACTOR

(71) Applicant: The Regents of the University of California, Oakland, CA (US)

(72) Inventors: Isha Jain, San Francisco, CA (US); Xuewen Chen, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 219 days.

(21) Appl. No.: 16/743,836

(22) Filed: Jan. 15, 2020

Related U.S. Application Data

(60) Provisional application No. 62/792,758, filed on Jan. 15, 2019.

(51) Int. Cl.
*A61K 31/51* (2006.01)
*A61B 5/1455* (2006.01)

(52) U.S. Cl.
CPC .......... *A61K 31/51* (2013.01); *A61B 5/14551* (2013.01)

(58) Field of Classification Search
None
See application file for complete search history.

(56) References Cited

U.S. PATENT DOCUMENTS

| | | | |
|---|---|---|---|
| 6,140,081 A | 10/2000 | Barbas | |
| 6,453,242 B1 | 7/2002 | Eisenberg et al. | |
| 6,534,261 B1 | 3/2003 | Cox et al. | |
| 7,888,121 B2 | 2/2011 | Urnov et al. | |
| 7,972,854 B2 | 7/2011 | Miller et al. | |
| 2005/0085498 A1* | 4/2005 | Byrd | A61P 9/00 514/565 |
| 2011/0145940 A1 | 6/2011 | Voytas et al. | |
| 2016/0355797 A1 | 12/2016 | Konermann et al. | |

FOREIGN PATENT DOCUMENTS

| | | | |
|---|---|---|---|
| WO | WO9853058 | 11/1998 | |
| WO | WO9853059 | 11/1998 | |
| WO | WO9853060 | 11/1998 | |
| WO | WO02016536 | 2/2002 | |
| WO | WO03016496 | 2/2003 | |
| WO | WO-2017027810 A2 * | 2/2017 | ............. A61K 31/19 |

OTHER PUBLICATIONS

Whitfield, K.C. et al. 2018. Thiamine deficiency disorders: diagnosis, prevalence, and a roadmap for global control programs. Annals of the New York Academy of Sciences 1430: 3-43; specif. pp. 5, 7, 12.*
Hazell, A.S. et al. 2009. Update of cell damage mechanisms in thiamine deficiency: focus on oxidative stress, excitotoxicity and inflammation. Alcohol & Alcoholism 44(2): 141-147; specif. pp. 141, 142.*
Bayer, U. et al. 2017. Intermittent hypoxic-hyperoxic training on cognitive performance in geriatric patients. Alzheimer's & Dementia: Translational Research & Clinical Interventions 3: 114-122; specif. pp. 114, 115, 121.*
Budinger, G.R.S. et al. 2013. Balancing the risks and benefits of oxygen therapy in critically ill adults. CHEST 143(4): 1151-1162; specif. pp. 1151, 1153.*
Bardaweel, S.K. et al. 2018. Reactive oxygen species: the dual role in physiological and pathological conditions of the human body. Eurasian Journal of Medicine 50(3): 193-201; specif. pg. 193.*
Desjardins, P. et al. 2005. Role of mitochondrial dysfunction and oxidative stress in the pathogenesis of selective neuronal loss in Wernicke's encephalopathy. Molecular Neurobiology 31: 17-25; specif. pp. 17, 19.*
Jain, I.H. et al. 2016. Hypoxia as a therapy for mitochondrial disease. Science 352(6281): 54-61; specif. pp. 58, 59.*
Ferrari, M. et al. May 8, 2017. Hypoxia treatment reverses neurodegeneratvie disease in a mouse model of Leigh syndrome. Proceedings of the National Academy of Sciences (PNAS), pp. E4241-E4250; specif. pp. E4241, E4252.*
Arroyo et al. (2016) "A Genome-wide CRISPR Death Screen Identifies Genes Essential for Oxidative Phosphorylation" Cell Metab. 24(6): 875-885.
Blass et al. (1988) "Thiamine and Alzheimer's Disease—A Pilot Study" Archives of Neurology 45(8): 833-835.
Brown et al. (1993) "Diet and Refsum's disease. The determination of phytanic acid and phytol in certain foods and the application of this knowledge to the choice of suitable convenience foods for patients with Refsum's disease" J. Hum. Nutr. Diet. 6(4): 295-305.
Costantini et al. (2013) "High-dose thiamine as initial treatment for Parkinson's disease" Case Reports bcr2013009289, pp. 1-4.
Dinicolantonio et al. (2018) "Thiamine and Cardiovascular Disease: A Literature Review" Progress in Cardiovascular Diseases 61(1): 27-32.
Easter et al. (2014) "Thiamine Deficiency : A Case Presentation and Literature Review" Case Reports 6(4): 1-6.

(Continued)

*Primary Examiner* — Adam Weidner
*Assistant Examiner* — Sharon M. Papciak
(74) *Attorney, Agent, or Firm* — Edward J. Baba; Shweta Chandra; Bozicevic, Field & Francis LLP

(57) ABSTRACT

The present disclosure provides methods of alleviating a symptom or delaying disease progression of a condition associated with a thiamine deficiency, a thiamine-dependent enzyme, or an associated cofactor and/or treating a condition associated with a thiamine deficiency, a thiamine-dependent enzyme, or an associated cofactor. The present methods result in alleviating a symptom or delaying disease progression of the condition associated with the thiamine deficiency, the thiamine-dependent enzyme, or the associated cofactor, treatment of the condition associated with the thiamine deficiency, the thiamine-dependent enzyme, or the associated cofactor, and/or alteration of a phenotypic characteristic of the condition associated with the thiamine deficiency, the thiamine-dependent enzyme, or the associated cofactor.

18 Claims, 6 Drawing Sheets

(56) References Cited

OTHER PUBLICATIONS

Finsterer et al. (2018) "Biomarkers for Detecting Mitochondrial Disorders" J. Clin. Med. 7(16): 1-9.
Flynn et al. (2015) "Wernicke's Encephalopathy: Increasing Clinician Awareness of This Serious, Enigmatic, Yet Treatable Disease" Prim. Care Companion CNS Disord. 17(3): 1-19.
Gibson et al. (2013) "Abnormal thiamine-dependent processes in Alzheimer's Disease. Lessons from diabetes" Molecular and Cellular Neuroscience 55: 17-25.
Harper et al. (1986) "Clinical signs in the Wernicke-Korsakoff complex: A retrospective analysis of 131 cases diagnosed at necropsy" J. Neurol. Neurosurg. Psychiatry 49(4): 341-345.
Hazell et al. (1998) "Mechanisms of neuronal cell death in Wernicke's encephalopathy" Metab. Brain Dis. 13(2): 97-122.
Jain et al. (2016) "Hypoxia as a therapy for mitochondrial disease" Science 352(6281): 54-61.
Jakkamsetti et al. (2019) "Brain metabolism modulates neuronal excitability in a mouse model of pyruvate dehydrogenase deficiency" Science Translational Medicine 11(480): 1-16.
Jauhari et al. (2017) "Thiamine Responsive Pyruvate Dehydrogenase Complex Deficiency: A Potentially Treatable Cause of Leigh's Disease" J. Pediatr. Neurosci. 12(3): 265-267.
Jhala et al. (2011) "Modeling neurodegenerative disease pathophysiology in thiamine deficiency: Consequences of impaired oxidative metabolism" Neurochemistry International 58: 248-260.
Kim et al. (2006) "HIF-1-mediated expression of pyruvate dehydrogenase kinase: a metabolic switch required for cellular adaptation to hypoxia." Cell Metab. 3(3): 177-185.
Lake et al. (2015) "Leigh syndrome: neuropathology and pathogenesis.," J. Neuropathol. Exp. Neurol. 74(6): 482-492.
Langlais (1995) "Pathogenesis of Diencephalic Lesions in an Experimental Model of Wernicke's Encephalopathy" Metab. Brain Dis. 10(1): 31-44.
Liang et al. (2015) "Metformin Is a Substrate and Inhibitor of the Human Thiamine Transporter, THTR-2 (SLC19A3)" Molecular Pharmaceutics 12(12): 4301-4310.
Lichtman et al. (1974) "Effect of Propranolol on Oxygen Binding to Hemoglobin In Vitro and In Vivo" Circulation 49(5): 881-885.
Lonsdale (2015) "Thiamine and magnesium deficiencies: Keys to disease" Med. Hypotheses 84(2): 129-134.
Mayr et al. (2014) "Lipoic acid biosynthesis defects," J. Inherit. Metab. Dis. 37(4): 553-563.
O'Donnell (2017) "Lactic Acidosis: A Lesser Known Side Effect of Thiamine Deficiency" Practical Gastroenterology, pp. 24-32.
Page et al. (2011) "Thiamine deficiency in diabetes mellitus and the impact of thiamine replacement on glucose metabolism and vascular disease" International Journal of Clinical Practice 65(6): 684-690.
Papandreou et al. (2006) "HIF-1 mediates adaptation to hypoxia by actively downregulating mitochondrial oxygen consumption" Cell Metab. 3(3): 187-197.
Paredes et al. (2018) "Poldip2 is an oxygen-sensitive protein that controls PDH and αKGDH lipoylation and activation to support metabolic adaptation in hypoxia and cancer" Proc. Natl. Acad. Sci. 115(8): 1789-1794.
Patel et al. (2012) "The Spectrum of pyruvate dehydrogenase complex deficiency: Clinical, biochemical and genetic features in 371 patients," Mol. Genet. Metab. 105(1): 34-43.
Quaegebeur et al. (2016) "Deletion or inhibition of the oxygen sensor PHD1 protects against ischemic stroke via reprogramming of neuronal metabolism" Cell Metab. 23(2): 280-291.
Quinlan et al. (2014) "The 2-oxoacid dehydrogenase complexes in mitochondria can produce superoxide/hydrogen peroxide at much high rates than complex I," J. Biol. Chem. 289(12): 8312-8325.
Sidhu et al. (2008) "Tissue-specific pyruvate dehydrogenase complex deficiency causes cardiac hypertrophy and sudden death of weaned male mice" Am. J. Physiol. Hear. Circ. Physiol. 295(3): H946-H952.
Sun et al. (2014) "Hypoxic regulation of glutamine metabolism through HIF1 and SIAH2 supports lipid synthesis that is necessary for tumor growth" Cell Metab. 19(2): 285-292.
Taivassalo et al. (2002) "Venous oxygen levels during aerobic forearm exercise: An index of impaired oxidative metabolism in mitochondrial myopathy" Ann. Neurol. 51(1): 38-44.
Vafai et al. (2012) "Mitochondrial disorders as windows into an ancient organelle" Nature 491(7424): 374-383.
Vetreno et al. (2012) "Brain and behavioral pathology in an animal model of Wernicke's encephalopathy and Wernicke-Korsakoff syndrome" Brain Res. 1436: 178-192.
Vinh Quoc Lu'o'ng et al. (2011) "Role of Thiamine in Alzheimer's Disease" American Journal of Alzheimer's Disease & Other Dementias 26(8): 588-598.
Vinh Quoc Lu'o'ng et al. (2012) "The Impact of Thiamine Treatment in the Diabetes Mellitus" Journal of Clinical Medicine Research 4(3): 153-160.
Watanabe (1978) "Pyrithiamine-induced acute thiamine-deficient encephalopathy in the mouse" Exp. Mol. Pathol. 28(3): 381-394.
Yeaman (1986) "The mammalian 2-oxoacid dehydrogenases: a complex family" Trends Biochem. Sci. 11(7): 293-296.
Zhang et al. (2012) "Thiamine Nutritional Status and Depressive Symptoms Are Inversely Associated among Older Chinese Adults" The Journal of Nutrition 143(1): 53-58.
Johnson et al. (2001) "Inactivation of the murine pyruvate dehydrogenase (Pdha1) gene and its effect on early embryonic development" Mol. Genet. Metab. 74(3): 293-302.

\* cited by examiner

17ppm (control)

0ppm (thiamine deficiency)

METHODS OF TREATING CONDITIONS RELATED TO A THIAMINE DEFICIENCY, A THIAMINE-DEPENDENT ENZYME, OR AN ASSOCIATED COFACTOR

CROSS-REFERENCE

This application claims the benefit of U.S. Provisional Patent Application No. 62/792,758, filed Jan. 15, 2019, which application is incorporated herein by reference in its entirety.

STATEMENT REGARDING FEDERALLY SPONSORED RESEARCH

This invention was made with government support under grant no. OD026398 awarded by the National Institutes of Health. The government has certain rights in the invention.

INTRODUCTION

Thiamin pyrophosphate (TPP), the active form of thiamine, is involved in several enzyme functions associated with the metabolism of carbohydrates, branched-chain amino acids, and fatty acids. Thiamine deficiency or mutations in any of the genes involved in metabolism of a thiamine-dependent enzyme or an associated cofactor (e.g. lipoic acid) can lead to diseases including, but not limited to, Wernicke-Korsakoff syndrome, wet Beriberi, dry Beriberi, pyruvate dehydrogenase complex (PDHC) deficiency, maple syrup urine disease, thiamine-responsive megaloblastic anemia, and Biotin-responsive basal ganglia disease. Prolonged thiamine deficiency may lead to Wernicke-Korsakoff Syndrome (WKS), which causes severe and incurable intellectual disability. There are currently no available therapies that work consistently for WKS or any of the related genetic conditions.

The methods disclosed herein address the above limitations and fulfill other needs.

SUMMARY

The present disclosure generally provides methods of delaying disease progression or alleviating a symptom of a condition associated with a thiamine deficiency, a thiamine-dependent enzyme, or an associated cofactor (e.g. lipoic acid) and/or treating a condition associated with a thiamine deficiency, a thiamine-dependent enzyme, or an associated cofactor (e.g. lipoic acid). The present methods result in alleviating a symptom or delaying disease progression of the condition associated with the thiamine deficiency, the thiamine-dependent enzyme, or the associated cofactor (e.g. lipoic acid), treatment of the condition associated with the thiamine deficiency, the thiamine-dependent enzyme, or the associated cofactor (e.g. lipoic acid), and/or alteration of a phenotypic characteristic of the condition associated with the thiamine deficiency, the thiamine-dependent enzyme, or the associated cofactor (e.g. lipoic acid).

Provided herein is a method of alleviating a symptom or delaying disease progression of a condition associated with a thiamine deficiency, a thiamine-dependent enzyme, or an associated cofactor (e.g. lipoic acid), the method including administering a reduced level of oxygen at a set interval for a set time period. In some embodiments, the reduced level of oxygen results in alleviating the symptom of the condition associated with the thiamine deficiency, the thiamine-dependent enzyme, or the associated cofactor (e.g. lipoic acid). In some embodiments, the methods described herein include administering a reduced level of oxygen relative to a normal level.

Also provided herein is a method of treating a condition associated with a thiamine deficiency, a thiamine-dependent enzyme, or an associated cofactor (e.g. lipoic acid), the method including administering a reduced level of oxygen at a set interval for a set time period. In some embodiments, the reduced level of oxygen results in treating the condition associated with the thiamine deficiency, the thiamine-dependent enzyme, or the associated cofactor (e.g. lipoic acid). In some embodiments, the methods described herein are performed in an individual. In some embodiments, the methods described herein include administering a reduced level of oxygen relative to a normal level.

In some embodiments, the condition associated with the thiamine deficiency, the thiamine-dependent enzyme, or the associated cofactor (e.g. lipoic acid) includes Pyruvate Dehydrogenase Deficiency, Oxoglutarate Dehydrogenase Deficiency, Maple Syrup Urine Disease, Multiple Mitochondrial Deficiencies, Amish Lethal Microencephaly, Wernicke-Korsakoff Syndrome, Wernicke encephalopathy, Korsakoff syndrome, wet Beriberi, dry Beriberi, Lipoic Acid Synthetase Deficiency, defects of thiamine transport, and defects of transketolase activity. In some embodiments, the gene associated with the condition associated with the thiamine deficiency, the thiamine-dependent enzyme, or the associated cofactor (e.g. lipoic acid) includes. SLC19A2, SLC19A3, SLC25A19, SLC22A1, SLC22A3, PDHA1, PDHB, DLAT, DLD, PDHX, OGDH, DLST, BCKDHA, BCKDHB, DBT, MECR, MCAT, OXSM, LIAS, NFU1, BOLA3, IBA57, GLRX5, TPK1, HACL1, TKTL1, and TKT. In some embodiments, the condition associated with the thiamine deficiency, the thiamine-dependent enzyme, or the associated cofactor (e.g. lipoic acid) is Wernicke-Korsakoff Syndrome. In some embodiments, the condition associated with the thiamine deficiency, the thiamine-dependent enzyme, or the associated cofactor (e.g. lipoic acid) is wet Beriberi or dry Beriberi. In some embodiments, the method further includes diagnosing the condition associated with the thiamine deficiency, the thiamine-dependent enzymes, or the associated cofactor (e.g. lipoic acid).

In some embodiments, the reduced level of oxygen includes an oxygen deficiency. In some embodiments, the reduced level of oxygen is hypoxia. In some embodiments, the method alters a phenotypic characteristic of the condition associated with the thiamine deficiency, the thiamine-dependent enzyme, or the associated cofactor (e.g. lipoic acid). In such embodiments, the phenotypic characteristic is encephalopathy, congestive heart failure, muscle atrophy, ophthalmoplegia, ataxia, confusion, vision change, loss of memory, hallucination, confabulation, inability to form new memories, or sleep disturbances. See, e.g., Dhir, S. et al. (2019). Frontiers in psychiatry, 10, 207.

In some embodiments, the method further includes administering an effective amount of thiamine. In such embodiments, the method further includes altering a phenotypic characteristic of the condition associated with the thiamine deficiency, the thiamine-dependent enzymes, or the associated cofactor (e.g. lipoic acid). In such embodiments, the condition associated with the thiamine deficiency, the thiamine-dependent enzymes, or the associated cofactor (e.g. lipoic acid) is Wernicke-Korsakoff Syndrome or wet Beriberi or dry Beriberi.

In some embodiments, the level of oxygen is measured by a pulse oximeter. In some embodiments, administering a reduced level of oxygen includes administering about 5-21% oxygen, such as 5-10% oxygen, 5-15% oxygen, 5-18% oxygen, 5-19%, or 5-20% oxygen.

In some embodiments, the set interval is once a day. In some embodiments, the set interval is twice a day. In some embodiments, the set interval is three times a day. In some embodiments, the set interval is continuous. In some embodiments, the set interval may be set by an individual.

In some embodiments, the set time period is 1-10 days. In some embodiments, the set time period is 5-15 days. In some embodiments, the set time period is 10-20 days. In some embodiments, the set time period is 15-25 days. In some embodiments, the set time period is 20-30 days. In some embodiments, the set time period is 30-60, 60-90, 90-120, 120-150, 150-180, 180-210, 210-240, 240-270, 270-300, 300-330 or 330-365 days. In certain embodiments, the set time period is 1-2, 2-3, 3-4, 4-5, 5-10, 10-15, 15-20, 20-25, 25-50, 50-75 or 75-100 years. In other embodiments, the set time period is continuous or for 24 hours a day. In some embodiments, the set time period may be set by an individual.

BRIEF DESCRIPTION OF THE DRAWINGS

The accompanying drawings, which are incorporated herein, form part of the specification. Together with this written description, the drawings further serve to explain the principles of, and to enable a person skilled in the relevant art(s), to make and use the present invention.

DEFINITIONS

Figure 1:
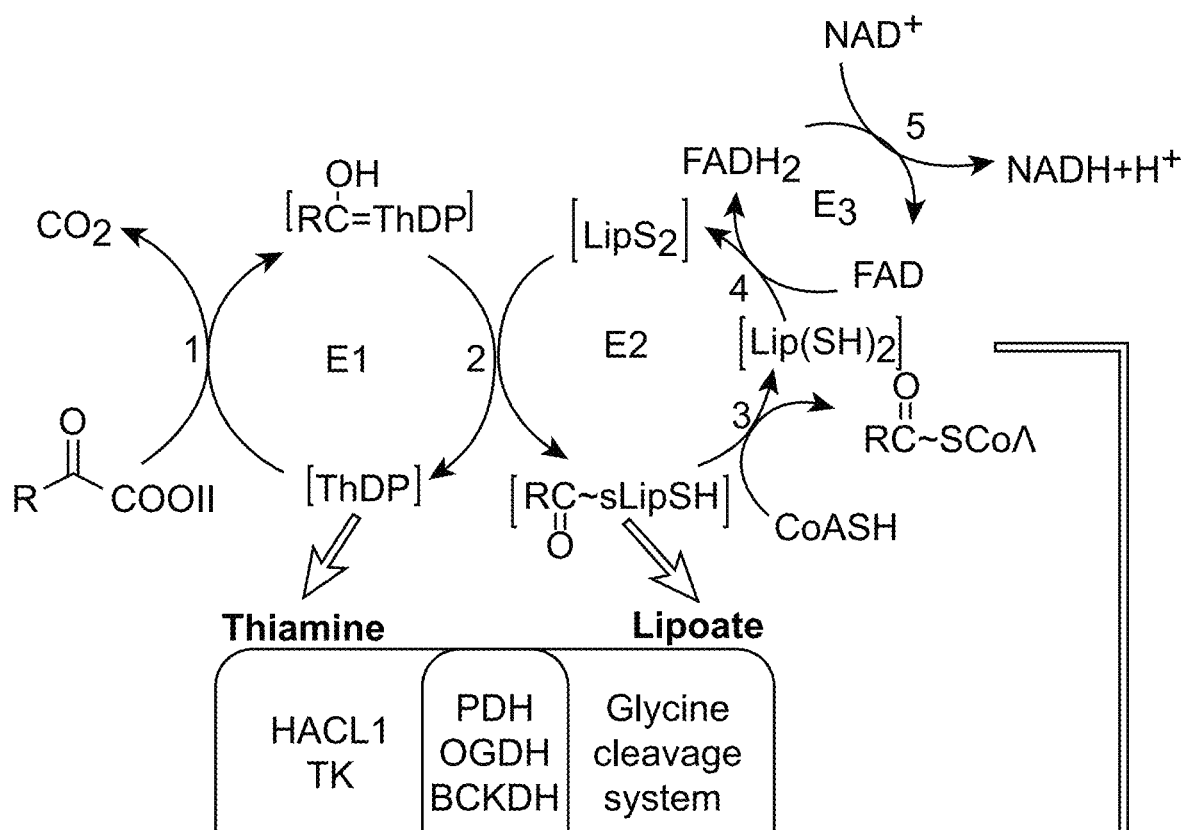
FIG. 1 depicts the structure and enzymatic mechanisms of exemplary thiamine-dependent enzymes such as 2-oxoacid dehydrogenases.
Figure 1:
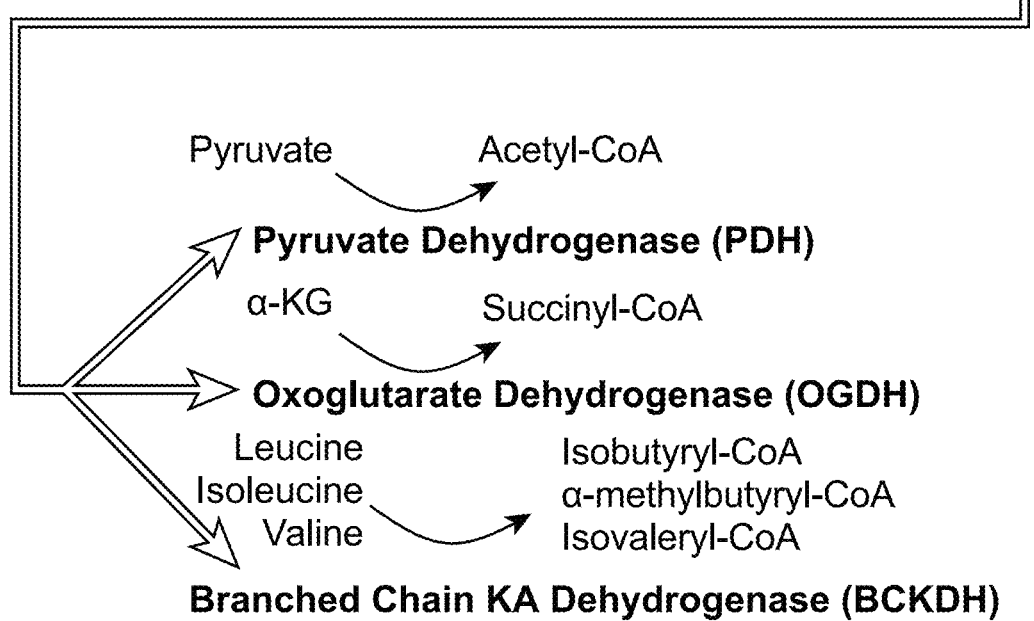

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As used herein, a "condition related to a thiamine deficiency, a thiamine-dependent enzyme, or an associated cofactor (e.g. lipoic acid)" or "a condition associated with a thiamine deficiency, a thiamine-dependent enzyme, or an associated cofactor (e.g. lipoic acid)" means any disease or other deleterious condition in which a thiamine deficiency, a thiamine-dependent enzyme (e.g. a 2-oxoacid dehydrogenase), or an associated cofactor (e.g. lipoic acid), is known or suspected to play a role. Examples of conditions related to a thiamine deficiency, a thiamine-dependent enzyme, or an associated cofactor (e.g. lipoic acid), or a condition associated with a thiamine deficiency, a thiamine-dependent enzyme, or an associated cofactor (e.g. lipoic acid) include Pyruvate Dehydrogenase Deficiency, Oxoglutarate Dehydrogenase Deficiency, Maple Syrup Urine Disease, Multiple Mitochondrial Deficiencies, Amish Lethal Microencephaly, Wernicke-Korsakoff Syndrome, Wernicke encephalopathy, Korsakoff syndrome, wet Beriberi, dry Beriberi, Lipoic Acid Synthetase Deficiency, defects of thiamine transport, defects of transketolase activity, and the like.

The terms "subject," "individual," "host," and "patient" are used interchangeably herein to a member or members of any mammalian or non-mammalian species. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, particularly mammals, e.g. a non-human primate, a murine (e.g., a mouse, a rat), lagomorpha, etc. may be used for experimental investigations.

The term "biocompatible," as used herein, refers to a property of a material that allows for prolonged contact with a tissue in a subject without causing toxicity or significant damage.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease and/or delaying disease progression. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "target," as used in reference to a tissue or site, refers to a tissue or location within a subject's body to which an active agent is, or is intended to be, delivered by an implant of the present disclosure. The target tissue can include pathological tissue, e.g., cancerous tissue, that is to be treated by the active agent, or can include tissue where occurrence or recurrence of pathology, e.g., cancer, is to be prevented or delayed. A "non-target tissue" may refer to any tissue that is not the intended target for delivering an active agent using the implant. In some cases, the non-target tissue is a tissue that is adjacent the target tissue. In some cases, the non-target tissue includes a systemically circulating tissue, such as blood.

As used herein, "altering" can mean being modified by at least 10%, 20%, 30%, 40%, 50%, 60%, 70%, 80%, 90%, or 100% relative to an initial value. In certain embodiments of the invention the phenotype is modified by at least 2, 3, 5, 10, 20, 50, or 100-fold relative to an initial value.

As used herein, a "phenotypic characteristic" can be any observable or detectable characteristic, property, attribute, or function of a cell. The phenotypic characteristic may be observed or detected in any of a number of ways. For example, a phenotypic characteristic may be observed or detected either by performing a test, observation, or measurement on the cell itself or by performing a test, observation, or measurement, on other cells, tissues, organs, etc., that may be affected by the cell, or by performing a test, observation, or measurement on a subject that contains the cell. The term "phenotypic characteristic" includes any "phenotypic characteristic" and also refers more broadly to characteristics, properties, attributes, functions, etc., that may result from a combination of two or more phenotypic characteristics. Certain of these phenotypic characteristics may be defined with respect to an effect that human cells exhibiting the phenotypic characteristic have on other cells or tissues either in vitro or in vivo.

As used herein, "alleviating" can mean being reduced by at least 10%, 20%, 30%, 40%, 50%, 60%, 70%, 80%, 90%, or 100% relative to an initial value. In certain embodiments of the invention the symptom is modified by at least 2, 3, 5, 10, 20, 50, or 100-fold relative to an initial value.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a symptom" includes a plurality of such symptoms and reference to "the symptom" includes reference to one or more symptoms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure generally provides methods of alleviating a symptom or delaying disease progression of a condition associated with a thiamine deficiency, a thiamine-dependent enzyme, or an associated cofactor (e.g. lipoic acid) and/or treating a condition associated with a thiamine deficiency, a thiamine-dependent enzyme, or an associated cofactor (e.g. lipoic acid). The present methods result in alleviating the symptom of the condition associated with the thiamine deficiency, the thiamine-dependent enzyme, or the associated cofactor (e.g. lipoic acid), treatment of the condition associated with the thiamine deficiency, the thiamine-dependent enzyme, or the associated cofactor (e.g. lipoic acid), and/or alteration of the phenotypic characteristic of the condition associated with the thiamine deficiency, the thiamine-dependent enzyme, or the associated cofactor (e.g. lipoic acid).

Provided herein is a method of alleviating a symptom or delaying disease progression of a condition associated with a thiamine deficiency, a thiamine-dependent enzyme, or an associated cofactor (e.g. lipoic acid), the method including administering a reduced level of oxygen at a set interval for a set time period. In some embodiments, the reduced level of oxygen results in alleviating the symptom of the condition associated with the thiamine deficiency, the thiamine-dependent enzyme, or the associated cofactor (e.g. lipoic acid).

Also provided herein is a method of treating a condition associated with a thiamine deficiency, a thiamine-dependent enzyme, or an associated cofactor (e.g. lipoic acid), the method including administering a reduced level of oxygen at a set interval for a set time period. In some embodiments, the reduced level of oxygen results in treating the condition associated with the thiamine deficiency, the thiamine-dependent enzyme, or the associated cofactor (e.g. lipoic acid). In some embodiments, the methods described herein are performed in an individual.

Conditions Associated with a Thiamine Deficiency, a Thiamine-Dependent Enzyme, or an Associated Cofactor (e.g. Lipoic Acid)

The present disclosure generally provides methods of alleviating a symptom or delaying disease progression of a condition associated with a thiamine deficiency, a thiamine-dependent enzyme, or an associated cofactor (e.g. lipoic acid) and/or treating a condition associated with a thiamine deficiency, a thiamine-dependent enzyme, or an associated cofactor (e.g. lipoic acid).

Figure 2:
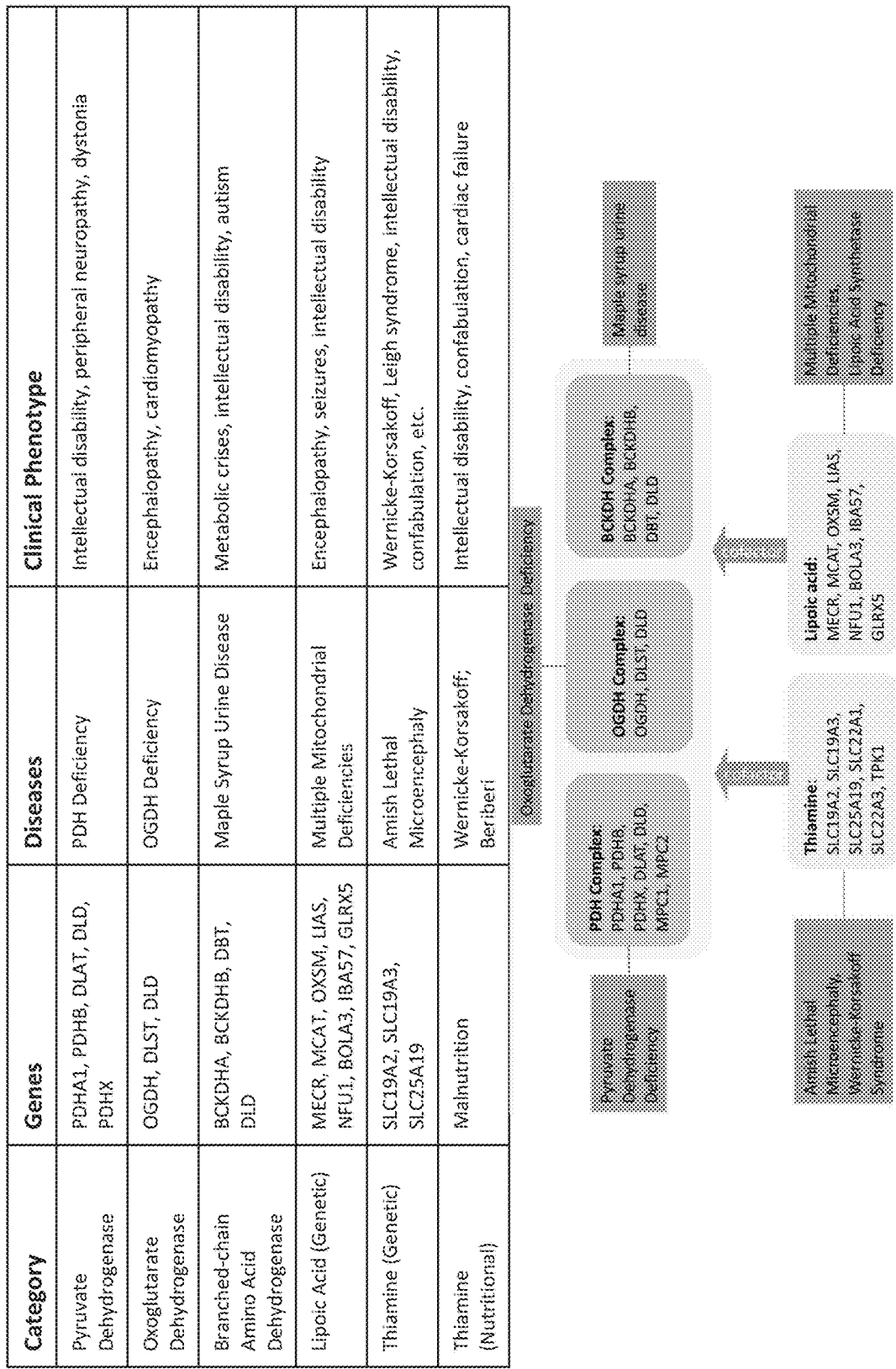
FIG. 2 depicts exemplary conditions associated with thiamine deficiency.

FIG. 1 characterizes the disease pathophysiology and depicts the structure and enzymatic mechanism of thiamine-dependent enzymes, three of the thiamine-dependent enzymes are Pyruvate Dehydrogenase (PDH), Oxoglutarate Dehydrogenase (OGDH) and Branched Chain Ketoacid Dehydrogenase (BCKDH), all of which require lipoic acid as a cofactor. Two additional known thiamine-dependent enzymes are hydroxyacyl-CoA lyase (HACL1) and transketolase (TKT). There are diseases associated with deprivation of thiamine, a related cofactor (lipoic acid) or any of the associated enzyme complexes (FIG. 2).

In some embodiments, the condition associated with the thiamine deficiency, the thiamine-dependent enzyme, or the associated cofactor (e.g. lipoic acid) includes Pyruvate Dehydrogenase Deficiency, Oxoglutarate Dehydrogenase Deficiency, Maple Syrup Urine Disease, Multiple Mitochondrial Deficiencies, Amish Lethal Microencephaly, Wernicke-Korsakoff Syndrome, Wernicke encephalopathy, Korsakoff syndrome, wet Beriberi, dry Beriberi, Lipoic Acid Synthetase Deficiency, defects of thiamine transport, and defects of transketolase activity. In some embodiments, the gene associated with the condition associated with the thiamine deficiency, the thiamine-dependent enzyme, or the associated cofactor (e.g. lipoic acid) includes SLC19A2, SLC19A3, SLC25A19, SLC22A1, SLC22A3, PDHA1, PDHB, DLAT, DLD, PDHX, OGDH, DLST, BCKDHA, BCKDHB, DBT, MECR, MCAT, OXSM, LIAS, NFU1, BOLA3, IBA57, GLRX5, TPK1, HACL1, TKTL1, and TKT. In some embodiments, the condition associated with the thiamine deficiency, the thiamine-dependent enzyme, or the associated cofactor (e.g. lipoic acid) is Wernicke-Korsakoff Syndrome or wet Beriberi or dry Beriberi.

In some embodiments, the subject methods further include altering a phenotypic characteristic of the condition associated with the thiamine deficiency, the thiamine-dependent enzyme, or the associated cofactor (e.g. lipoic acid). Examples of phenotypic characteristics include ophthalmoplegia, ataxia, confusion, vision change, loss of memory, hallucination, confabulation, inability to form new memories, encephalopathy, seizures, intellectual disability, intellectual disability, peripheral neuropathy, dystonia, cardiomyopathy, metabolic crises, parkinsonian phenotypes, autism spectrum disorders (see, e.g., Dhir, S. et al. (2019). Frontiers in psychiatry, 10, 207), Wernicke-Korsakoff, Leigh syndrome, and cardiac failure.

In certain embodiments, the subject methods may be combined with other methods known in the art. For example, the methods described herein may include administering an effective amount of thiamine. The subject methods may also include diagnosing the condition associated with the thiamine deficiency, the thiamine-dependent enzyme, or the associated cofactor (e.g. lipoic acid).

Levels of Oxygen

The present disclosure generally includes, in part, administering a reduced level of oxygen at a set interval for a set time period. In some embodiments, the reduced level of oxygen comprises an oxygen deficiency. In some embodiments, the reduced level of oxygen is hypoxia. In such embodiments, the level of oxygen may be measured by a pulse oximeter.

In some embodiments, administering a reduced level of oxygen includes administering about 5-21% oxygen, such as 5-10% oxygen, 5-15% oxygen, 5-18% oxygen, 5-19%, or 5-20% oxygen. In some embodiments, the method includes administering 5-10% oxygen. In some embodiments, the method includes administering 5-15% oxygen. In some embodiments, the method includes administering 5-18% oxygen. In some embodiments, the method includes administering 5-19% oxygen. In some embodiments, the methods described herein includes administering a reduced level of oxygen relative to a normal level of oxygen. As used herein, a normal level of oxygen is used to describe the ambient level of oxygen in the blood or tissue of an individual prior to being subjected to any of the methods described herein.

As used herein, the term "hypoxia" is the reduction or lack of oxygen in organs, tissues, or cells. This decrease of oxygen tension can be due to a reduced supply in oxygen (causes include insufficient blood vessel network, defective blood vessel, and anemia) or to an increased consumption of oxygen relative to the supply. The level of oxygen is at least lower or less than about 30%, including at least lower or less than about 20%, at least lower or less than about 10% and lower or less than about 5%. For example, the level of oxygen may be about 10, 9, 8, 7, 6, 5, 4, 3, 2, or 1%. Those of skill in the art are familiar with the measurement of oxygen levels in biological systems, and are also aware that oxygen measurements may be expressed in "mm Hg", wherein, for example, 10% $O_2$ is equal to 76 mmHg and 1% $O_2$ is equal to 7.6 mmHg.

In some embodiments, the three 2-oxoacid dehydrogenase complexes (PDH, OGDH, and BCKDH) are the gatekeepers of mitochondrial energy metabolism, allowing different nutrient sources to funnel into the electron transport chain. All three complexes perform decarboxylation reactions using a carefully coordinated set of enzymes that allow for substrate channeling. Each enzyme complex includes several dozen copies of three protein components, such as E1, E2 and E3. E3 or dihydrolipoamide dehydrogenase (DLD) is common to all three complexes, whereas E1 and E2 are specific to each 2-oxoacid dehydrogenase. To allow for this specific decarboxylation biochemistry to proceed, all three 2-oxoacid dehydrogenases require thiamine pyrophosphate (TPP) and lipoic acid as cofactors (FIG. 1). In such embodiments, nutritional or genetic deficiencies that perturb the production or availability of the cofactors also result in impaired enzyme function.

In some embodiments, low oxygen tensions result in overexpression of the pyruvate dehydrogenase kinase (PDK) enzymes, which phosphorylate and inactive PDH. Without intending to be bound by any particular theory, limiting the production of acetyl-coA in the mitochondrial matrix reduces the amount of superoxide produced at a halted electron transport chain. In some embodiments, low oxygen tensions or hypoxia may be used as a therapy for Wernicke's Syndrome and Pyruvate Dehydrogenase Deficiency.

In some embodiments, the reduced level of oxygen includes an oxygen deficiency. In some embodiments, the reduced level of oxygen is hypoxia. A reduced level of oxygen may be induced via methods known in the art. In some embodiments, the methods described herein may be performed inside a hypobaric chamber at a pressure level well above the pressure threshold at which decompression sickness becomes a risk factor. Hypobaric chambers are well known, and comprise a controlled, sealable environment within which the atmospheric pressure can be manipulated to create a low pressure environment within the chamber. The chamber can therefore be used at ground level to simulate pressure conditions encountered in flight, since pressure decreases as altitude increases. The reduced pressure is achieved by evacuating atmospheric gases from the chamber. To return the chamber to ambient pressure, atmospheric gases are reintroduced. In other embodiments, the methods described herein may be performed inside a normobaric hypoxia chamber. In some other embodiments, other methods to administer a reduced level of oxygen include embolization, vascular disrupting agents or anti-angiogenic agents individually or in combination. In some other embodiments, the methods described herein may involve any small molecule that causes tissue hypoxia, for example by decreasing oxygen delivery or increasing oxygen consumption. Non-limiting examples of small molecules that decrease the oxygen binding ability of hemoglobin or that cause tissue hypoxia include papaverine, dipyridamole (see, e.g., De-Paula, E. et al. (1992) Brazilian journal of medical and biological research 25 (6), 557-565) and propranolol (see, e.g., Lichtman, M. A. et al. (1974). Circulation, 49 (5), 881-886). In some embodiments, any method known in the art to cause tissue hypoxia may be implemented. In some other embodiments, any method known in the art that lower tissue oxygen levels may be used. For example, lower tissue oxygen levels may result from a lower concentration of hemoglobin or a decreased affinity of hemoglobin for oxygen.

In certain cases, the subject methods may involve a targeted nuclease. One example of a targeted nuclease that may be used in the subject methods is a TAL Nuclease ("TALN", TAL effector nuclease, or "TALEN"). A TALN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus Xanthomonas during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a zinc finger nuclease or "ZFN". ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include C2H2 zinc fingers, C3H zinc fingers, and C4 zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the FokI nuclease with a zinc finger DNA binding domain.

Another example of a targeted nuclease that finds use in the subject methods is a targeted Spo11 nuclease, a polypeptide comprising a Spo11 polypeptide having nuclease activity fused to a DNA binding domain, e.g. a zinc finger DNA binding domain, a TAL effector DNA binding domain, etc. that has specificity for a DNA sequence of interest. See, for example, U.S. Application No. 61/555,857, the disclosure of which is incorporated herein by reference.

Other non-limiting examples of targeted nucleases include naturally occurring and recombinant nucleases, e.g. CRISPR/Cas9, restriction endonucleases, meganucleases homing endonucleases, and the like. Examples of a CRISPER/Cas9 system may be found in, for example, Turan et al. (2016) and Geisinger et al. (2016), the disclosures of which are incorporated herein by reference.

Examples of RNA-guided endonucleases are CRISPR/Cas endonucleases (e.g., class 2 CRISPR/Cas endonucleases such as a type II, type V, or type VI CRISPR/Cas endonucleases). A suitable genome editing nuclease is a CRISPR/Cas endonuclease (e.g., a class 2 CRISPR/Cas endonuclease such as a type II, type V, or type VI CRISPR/Cas endonuclease). In some cases, a suitable RNA-guided endonuclease is a class 2 CRISPR/Cas endonuclease. In some cases, a suitable RNA-guided endonuclease is a class 2 type II CRISPR/Cas endonuclease (e.g., a Cas9 protein). In some cases, a genome targeting composition includes a class 2 type V CRISPR/Cas endonuclease (e.g., a Cpf1 protein, a C2c1 protein, or a C2c3 protein). In some cases, a suitable RNA-guided endonuclease is a class 2 type VI CRISPR/Cas endonuclease (e.g., a C2c2 protein; also referred to as a "Cas13a" protein). Also suitable for use is a CasX protein. Also suitable for use is a CasY protein.

In some cases, the genome-editing endonuclease is a Type II CRISPR/Cas endonuclease. In some cases, the genome-editing endonuclease is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, the Cas9 polypeptide used in a composition or method of the present disclosure is a *Staphylococcus aureus* Cas9 (saCas9) polypeptide. In some cases, the genome-editing endonuclease is a CasX or a CasY polypeptide. CasX and CasY polypeptides are described in Burstein et al. (2017) Nature 542:237.

Also suitable for use is an RNA-guided endonuclease with reduced enzymatic activity. Such an RNA-guided endonuclease is referred to as a "dead" RNA-guided endonuclease; for example, a Cas9 polypeptide that comprises certain amino acid substitutions such that it exhibits substantially no endonuclease activity, but such that it still binds to a target nucleic acid when complexed with a guide RNA, is referred to as a "dead" Cas9 or "dCas9." In some cases, a "dead" Cas9 protein has a reduced ability to cleave both the complementary and the non-complementary strands of a double stranded target nucleic acid. For example, a "nuclease defective" Cas9 lacks a functioning RuvC domain (i.e., does not cleave the non-complementary strand of a double stranded target DNA) and lacks a functioning HNH domain (i.e., does not cleave the complementary strand of a double stranded target DNA). Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "nuclease defective Cas9", "dead Cas9" or simply "dCas9." Other residues can be mutated to achieve the above effects (i.e. inactivate one or the other nuclease portions). As non-limiting examples, residues D10, G12, G17, E762, H840, N854, N863, H982, H983, A984, D986, and/or A987 of *Streptococcus pyogenes* Cas9 (or the corresponding amino acids of a Cas9 homolog) can be altered (i.e., substituted). In some cases, two or more of D10, E762, H840, N854, N863, and D986 of *Streptococcus pyogenes* Cas9 (or the corresponding amino acids of a Cas9 homolog) are substituted. In some cases, D10 and N863 of *Streptococcus pyogenes* Cas9 (or the corresponding amino acids of a Cas9 homolog) are substituted with Ala. Also, mutations other than alanine substitutions are suitable.

In some cases, the genome-editing endonuclease is an RNA-guided endonuclease (and it corresponding guide RNA) known as Cas9-synergistic activation mediator (Cas9-SAM). The RNA-guided endonuclease (e.g., Cas9) of the Cas9-SAM system is a "dead" Cas9 fused to a transcriptional activation domain (wherein suitable transcriptional activation domains include, e.g., VP64, p65, MyoD1, HSF1, RTA, and SET7/9) or a transcriptional repressor domain (where suitable transcriptional repressor domains include, e.g., a KRAB domain, a NuE domain, an NcoR domain, a SID domain, and a SID4X domain). The guide RNA of the Cas9-SAM system comprises a loop that binds an adapter protein fused to a transcriptional activator domain (e.g., VP64, p65, MyoD1, HSF1, RTA, or SET7/9) or a transcriptional repressor domain (e.g., a KRAB domain, a NuE domain, an NcoR domain, a SID domain, or a SID4X domain). For example, in some cases, the guide RNA is a single-guide RNA comprising an MS2 RNA aptamer inserted into one or two loops of the sgRNA; the dCas9 is a fusion polypeptide comprising dCas9 fused to VP64; and the adaptor/functional protein is a fusion polypeptide comprising: i) MS2; ii) p65; and iii) HSF1. See, e.g., U.S. Patent Publication No. 2016/0355797.

Duration

The present disclosure generally includes, in part, administering a reduced level of oxygen at a set interval for a set time period. In some embodiments, the set interval is once a day, twice a day, or three times a day. In some other embodiments, the set interval may be set by an individual. In some embodiments, the set interval is continuous. In some embodiments, the set time period ranges from about 1 day to 1 month, e.g., from about 1-10 days, 5-15 days, 10-20 days, 15-25 days, and 20-30 days. In other embodiments, the set time period is continuous or for 24 hours a day. In some embodiments, the set time period may be set by an individual. Various other settings may be customized, such as varying the intensity of administration based on a time of day, or increasing the intensity of administration when the individual does not react to a given administration within a set interval, where the duration of the interval may also be set by the individual.

Utility

The methods disclosed herein find use in any in vitro or in vivo application in which it is desirable to alleviate a symptom of a condition associated with a thiamine deficiency, a thiamine-dependent enzyme, or an associated cofactor (e.g. lipoic acid) and/or treat a condition associated with a thiamine deficiency, a thiamine-dependent enzyme, or an associated cofactor (e.g. lipoic acid). In some cases, the therapy is non-immunogenic and may be re-administered multiple times. In some cases, the therapy is long-lasting. In some cases, the therapy involves hypoxia and/or thiamine supplementation. The methods described herein may be used to treat WKS in individuals that are either unresponsive to thiamine or are otherwise looking for alternatives to thiamine administration, since thiamine administration is ineffective once disease has progressed to WKS. The methods described herein may be used to treat wet Beriberi or dry Beriberi.

For example, the subject methods may be used to treat a disorder, a disease, or medical condition in a subject. The subject methods provide a therapy for prevention and reversal of WKS lesions. If WKS lesions are diagnosed at an early stage, thiamine supplementation can reverse disease. However, for a subset of patients, the disease progresses to Korsakoff syndrome and leads to severe intellectual disability. This causes permanent and irreversible damage, eventually leading to death; there are no proven treatments for WKS. The subject methods also provide a therapy for wet Beriberi, dry Beriberi, pyruvate dehydrogenase (PDH) deficiency and related disorders of 2-oxoacid dehydrogenases.

The methods described herein also provide a better understanding of supplemental oxygen use in critical care. Such methods may involve evaluation of biomarkers of disease including, but not limited to, plasma lactate and partial pressure of oxygen in tissues.

In some embodiments, the methods described herein may involve a therapeutic agent. By a "therapeutic agent" it is meant an agent, e.g. siRNA, shRNA, miRNA, CRISPRi agents, peptide, polypeptide, suicide gene, etc., that has a therapeutic effect upon a cell or an individual, for example, that promotes a biological process to treat a medical condition, e.g. a disease or disorder. The terms "individual," "subject," "host," and "patient," are used interchangeably herein and refer to any human subject for whom diagnosis, treatment, or therapy is desired. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

Examples of therapeutic agents include agents, i.e., siRNAs, shRNAs, miRNAs, CRISPRi agents, peptides, or polypeptides, which alter cellular activity. Other examples of therapeutic agents include suicide genes, i.e., genes that promote the death of cells in which the gene is expressed. Non-limiting examples of suicide genes include genes that encode a peptide or polypeptide that is cytotoxic either alone or in the presence of a cofactor, e.g., a toxin such as abrin, ricin A, pseudomonas exotoxin, cholera toxin, diphtheria toxin, Herpes Simplex Thymidine Kinase (HSV-TK); genes that promote apoptosis in cells, e.g. Fas, caspases (e.g. inducible Caspase9) etc.; and genes that target a cell for ADCC or CDC-dependent death, e.g. CD20.

In some instances, the therapeutic agent alters the activity of the cell in which the agent is expressed. In other words, the agent has a cell-intrinsic effect. For example, the agent may be an intracellular protein, transmembrane protein or secreted protein that, when expressed in a cell, will substitute for, or "complement", a mutant protein in the cell. In other instances, the therapeutic agent alters the activity of cells other than cells in which the agent is expressed. In other words, the agent has a cell-extrinsic effect. For example, the integrated gene of interest may encode a cytokine, chemokine, growth factor, hormone, antibody, or cell surface receptor that modulates the activity of other cells.

The subject methods may be applied to any disease, disorder, or natural cellular process that would benefit from alleviating a symptom or delaying disease progression of a condition associated with a thiamine deficiency, a thiamine-dependent enzyme, or an associated cofactor (e.g. lipoic acid) and/or treating a condition associated with a thiamine deficiency, a thiamine-dependent enzyme, or an associated cofactor (e.g. lipoic acid). For example, the subject agents and methods find use in treating genetic disorders. Any genetic disorder that results from a single gene defect may be treated by the subject methods, including, for example, Pyruvate Dehydrogenase Deficiency, Oxoglutarate Dehydrogenase Deficiency, Maple Syrup Urine Disease, Multiple Mitochondrial Deficiencies, Amish Lethal Microencephaly, Wernicke-Korsakoff Syndrome, Wernicke encephalopathy, and Korsakoff syndrome, wet Beriberi, dry Beriberi, Lipoic Acid Synthetase Deficiency, defects of thiamine transport, defects of transketolase activity, and the like. In some embodiments, the gene associated with the condition associated with the thiamine deficiency, the thiamine-dependent enzyme, or the associated cofactor (e.g. lipoic acid) includes. SLC19A2, SLC19A3, SLC25A19, SLC22A1, SLC22A3, PDHA1, PDHB, DLAT, DLD, PDHX, OGDH, DLST, BCKDHA, BCKDHB, DBT, MECR, MCAT, OXSM, LIAS, NFU1, BOLA3, IBA57, GLRX5, TPK1, HACL1, TKTL1, and TKT.

The subject methods may be used to treat nervous system conditions and to protect the CNS against nervous system conditions, e.g. neurodegenerative diseases (see, e.g., Jhala, S. S. et al. (2011). Neurochemistry international, 58 (3), 248-260), including, for example, e.g. Parkinson's Disease (see, e.g., Costantini, A. et al. (2013). Case Reports, 2013, bcr2013009289), Alzheimer's Disease (see, e.g., vinh quoc Luong, K. et al. (2011). American Journal of Alzheimer's Disease & Other Dementias®, 26 (8), 588-598; Gibson, G. E. et al. (2013). Lessons from diabetes. *Molecular and Cellular Neuroscience,* 55, 17-25; Blass, J. P. et al. Archives of neurology, 45 (8), 833-835), Huntington's Disease, Amyotrophic Lateral Sclerosis (ALS), Spielmeyer-Vogt-Sjögren-Batten disease (Batten Disease), Frontotemporal Dementia with Parkinsonism, Progressive Supranuclear Palsy, Pick Disease, prion diseases (e.g. Creutzfeldt-Jakob disease), Amyloidosis, glaucoma, diabetic retinopathy, age related macular degeneration (AMD), and the like); neuropsychiatric disorders (e.g. anxiety disorders (e.g. obsessive compulsive disorder), mood disorders (e.g. depression) (see, e.g., Zhang, G., et al. (2012). The Journal of nutrition, 143 (1), 53-58), childhood disorders (e.g. attention deficit disorder, autistic disorders), cognitive disorders (e.g. delirium, dementia), schizophrenia, substance related disorders (e.g. addiction), alcoholic brain disease, eating disorders, and the like); channelopathies (e.g. epilepsy, migraine, and the like); lysosomal storage disorders (e.g. Tay-Sachs disease, Gaucher disease, Fabry disease, Pompe disease, Niemann-Pick disease, Mucopolysaccharidosis (MPS) & related diseases, and the like); autoimmune diseases of the CNS (e.g. Multiple Sclerosis, encephalomyelitis, paraneoplastic syndromes (e.g. cerebellar degeneration), autoimmune inner ear disease, opsoclonus myoclonus syndrome, and the like); cerebral infarction, stroke, traumatic brain injury, and spinal cord injury. In some embodiments, the subject methods may be used to treat Alzheimer's Disease. In certain embodiments, the subject methods may be used to treat diabetes (see, e.g., vinh quoc Luong, K. et al. (2012). Journal of clinical medicine research, 4 (3), 153; Page, G. L. J. et al. (2011). International journal of clinical practice, 65 (6), 684-690) or cardiovascular complications associated with diabetes (see, e.g., DiNicolantonio, J. J. et al. (2018). Progress in cardiovascular diseases, 61 (1), 27-32), systolic heart failure (see, e.g., DiNicolantonio, J. J. et al. (2018). Progress in cardiovascular diseases, 61 (1), 27-32) or obesity.

The subject methods may also be used as a therapy to treat thiamine deficiency caused by drugs. Non-limiting examples of drugs that cause secondary thiamine deficiency are Metformin (see, e.g., Liang, X. et al. (2015). Molecular pharmaceutics, 12 (12), 4301-4310), loop diuretics, oral contraceptives, Stavudine, Tricyclic Antidepressants. Additional non-limiting examples of drugs that cause thiamine deficiency can be found in the 'A-Z Guide to Drug-Herb-Vitamin Interactions' (2006) by Alan Gaby and Vora, B. et al. (2019). The American journal of clinical nutrition.

Various pharmaceutical compositions and techniques for their preparation and use are known to those of skill in the art in light of the present disclosure. For a detailed listing of suitable pharmacological compositions and techniques for their administration one may refer to the detailed teachings herein, which may be further supplemented by texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

Other examples of how the subject methods may be used to treat medical conditions are disclosed elsewhere herein, or would be readily apparent to the ordinarily skilled artisan. The subject methods may also be used to with nitrogen generators or hypoxic gas mixtures. The subject methods may further be used with agents that cause tissue hypoxia, including but not limited to GBT-440, a small molecule hemoglobin modifier which increases hemoglobin oxygen affinity.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Validation of Hypoxia Rescue in Primary Neurons and Patient Fibroblasts (Prophetic)

As depicted in FIG. 1, there were several classes of deficiencies related to 2-oxoacid dehydrogenases or their relevant cofactors/substrates: Patients could have (i) lesions in the protein components of the 2-oxoacid dehydrogenases themselves—(e.g. PDHA1, PDHB, PDHX, DLAT, OGDH, DLST, BCKDHA, BCKDHB, DBT or DLD); (ii) mutations in transporters for the corresponding 2-oxoacids (e.g. MPC1, MPC2, etc.); (iii) mutations in the mitochondrial fatty acid synthesis pathway which produced lipoic acid (MECR, MCAT, OXSM, NFU1, BOLA3, LIAS, LIPT1, etc.); (iv) genetic defects in thiamine transport or processing (SLC19A2, SLC19A3, TPK1); and/or (v) direct dietary thiamine deficiency, which may alter the function of all 2-oxoacid dehydrogenases.

Genetic lesions related to 2-oxoacid dehydrogenases which may be candidates for hypoxia therapy in future studies will be broadly prioritized (FIG. 2). More specifically, the CRISPR-Cas9 system will be used with 2 guide RNAs targeting each gene to generate knockouts for lesions mentioned above. This will be done in primary cortical neurons obtained from E14-15 mice or in iPSC-derived neurons, as described in Quaegebeur et al. Upon confirming the knockout of a given gene, relative viability of each cell population will be measured as a function of oxygen tension. Triplicate primary neuron cultures (from three different mice) will be used, with triplicate technical replicates for each culture batch. Viability will be measured using trypan blue and overall cell number after 3 days in 0.1%, 1%, 3%, 5%, 10% and 21% 02. These experiments will be performed in tissue culture incubators which have been adapted for varying oxygen tensions using an oxygen sensor and electronic feedback loop (Thermo Heracell).

As a more directly disease-relevant model, patient-derived fibroblasts for genetic lesions where such samples are available (e.g. BCKDHA mutations) will also be obtained through the Coriell Institute Biobank. Cell viability and proliferation will be measured as a function of oxygen in the same conditions as described above for primary neurons (triplicate experimental replicates, using healthy patient fibroblasts as controls).

Primary neurons taken from WT animals at E14-15 and WT patient fibroblasts will be exposed to thiamine-deficient conditions (DMEM without thiamine, or with 10 μM thiamine), and viability and cell proliferation will be measured in varying oxygen tensions (same oxygen tensions and experimental conditions as above). Experiments will be done using 10% dialyzed FBS to prevent any trace amounts of thiamine from serum.

Example 2: Bioenergetic and Redox Characterization of 2-Oxoacid Dehydrogenases in Varying $O_2$ (Prophetic)

To better understand which genetic lesions can be rescued by hypoxia therapy, commonalities in their metabolic defects will be determined by characterizing oxygen consumption, superoxide production, flux through each 2-oxoacid dehydrogenase, and the role of the hypoxia transcriptional (HIF) program in the hypoxic rescue of each genetic lesion.

Oxygen consumption will be measured using the Seahorse assay in the primary neuron models of each genetic and nutritional deficiency. This will be done in triplicate neuronal cultures (from 3 separate mice per group), with triplicate technical replicates. Oxygen consumption will be measured as a function of ambient oxygen levels, by placing the seahorse machine in an enclosed plastic chamber which has varying oxygen tensions (0.1%, 1%, 3%, 5%, 10% and 21% $O_2$) being flushed through the enclosure.

To assess the relative superoxide production, Amplex Red and MitoSox assays will be used to measure mitochondrial and cytosolic superoxide/hydrogen peroxide production as a function of oxygen (same oxygen tensions and experimental conditions as in growth assays).

The current literature supports different mechanisms by which the different 2-oxoacid dehydrogenases limit activity during hypoxia. Most relevant to physiological function is the overall flux through each enzyme complex. Therefore, isotopically labeled substrates (C13-labeled pyruvate, glucose, branched chain amino acids and glutamine obtained through Cambridge Isotope Labs Inc.) will be used to measure flux through each of the 2-oxoacid dehydrogenases in all the genetic and nutrient models of disease used above (primary neurons). To ensure that the direct flux is captured through the different complexes, a rapid time-course of measurements (1m, 15m, 45m, 2h) will be performed. All metabolites will be measured through the University of Utah metabolomics core.

A component of hypoxia exposure is activation of the hypoxia transcriptional program. There are currently small molecules in Phase 4 clinical trials that artificially activate the HIF response by inhibiting the upstream prolyl hydroxylase enzymes (e.g. FG-4592). It will be determined whether the hypoxia response is sufficient to rescue the lesions identified above. If the hypoxic rescue is via the HIF response, this will enable even more rapid clinical translation using existing small molecules. Genetic and nutrient models will be exposed to 40 μM FG-4592 (or vehicle), which is a prolyl-hydroxylase inhibitor that is known to activate the hypoxia response, even when ambient oxygen levels are relatively high. Survival and growth will be assessed as described above.

Example 3: Hypoxia Therapy for Wernicke-Korsakoff Syndrome

A moderate and severe disease model were established for Wernicke's and Korsakoff syndrome. Historically, two different mouse models have been developed for Wernicke-Korsakoff syndrome. In the first case, mice are fed a thiamine-deficient diet and after 3-4 weeks on this diet, internal thiamine stores are depleted. This leads to onset of symptoms and death shortly afterwards. The second, more common model, relies on feeding a thiamine-deficient diet, in combination with daily administration of pyrithiamine. Pyrithiamine is an inhibitor of thiamine pyrophosphokinase which is responsible for converting dietary thiamine to the active form, thiamine pyrophosphate. In this model, animals display weight loss by day 10, ataxia a few days later, seizures at day 16 and death shortly after. Disease progression in both models can be reversed by administration of 500 mg thiamine 3×/day. Furthermore, rodent models of thiamine deficiency (TD) share many features with the human clinical presentation-ataxia, loss of consciousness, nystagmus, seizures and dementia-like symptoms.

Both models of TD were characterized and additionally a model of more moderate disease will be established to better reflect the rate of disease progression in humans. More specifically, WT mice were given a diet of 0 ppm, 1 ppm or 17 ppm thiamine. 15 mice were used for each cohort to give 80% power to detect a 50% difference in survival between untreated, moderate and severe disease conditions. For each thiamine dose, vehicle or 500 μg/kg of pyrithiamine was administered daily. In all 6 cohorts, daily body weight will be monitored, frequency of seizures will be recorded using an accelerometer (DSI Inc.), weekly behavior tests (rotarod and open field) and track survival (due to natural death or until euthanasia criteria have been reached) were performed. If needed, alternate low doses of thiamine were used to create an intermediate disease model. Once a regimen that results in slower disease progression is established, a second set of experiments will be performed, where 500 mg thiamine is administered 3×/day to mice that show (a) no disease, (b) moderate disease and (c) severe disease. It will be monitored whether the aforementioned phenotypes can be reversed starting day 10 of treatment. The goal is to also establish a model of WK syndrome, where therapeutic doses of thiamine are provided, however permanent damage has already ensued.

Hypoxia and moderate hyperoxia exposure were tested in these mouse models of WK syndrome. Six groups of mice for each different oxygen exposure will be used—(no disease, moderate disease, extreme disease)×(with or without thiamine treatment starting day 10 of the disease model). Each of these cohorts will have 10 mice/group per oxygen tension—10%, 21% or 50% $FiO_2$. This sample size should be sufficient to detect a 30% increase in survival with 80% power. Disease progression in these different conditions will be carefully monitored. Daily body weights from the beginning of treatment will be taken. Additionally, behavior was monitored on a weekly basis using rotarod tests, open field experiments and the Y-maze memory test. For 3 mice per group, T2-weighted MRI scans was performed once per week. This will allow the monitoring of the disease progression and reversal. For a separate set of 3 mice per group, mice were sacked, and neuropathology performed, staining for neuronal cell loss (using NeuN) or neuroinflammatory signatures (using antibodies against GFAP) similar to that performed in Jain et. al.

Enzyme activity in intact tissue will be measured. In the same group of mice used for neuropathology, skeletal muscle and brain tissue will be flash frozen (using the hemisphere that was not used for neuropathology). Enzyme activity for all three 2-oxoacid dehydrogenases will be measured to determine the extent of enzyme dysfunction and whether the activity itself is affected by exposed oxygen tensions. Enzyme activities will be measured in flash frozen tissue using a colorimetric readout of NADH production using the relevant substrates. This will be done in triplicate experimental replicates (from three mice per group) and triplicate technical replicates.

Example 4: Hypoxia Therapy for PDH Deficiency (Prophetic)

The effects of varying oxygen tensions will be tested on the brain/heart/skeletal muscle model of PDH deficiency. PDHA1 is located on the X chromosome. Therefore, male mice with a single loss-of-copy for PDHA1 have no remaining enzyme activity and are embryonic lethal. However, males with brain, heart and skeletal-muscle-specific knockout survive until weaning. Upon weaning, these diseased mice with heart or skeletal-muscle-specific PDH deficiency die within 7 days of sudden heart failure. The exact pathology remains to be studied, but the striking effect on survival upon changes in fuel sources is in line with the metabolic role of PDC in shuttling glucose-derived carbons into the electron transport chain. Ten knockout mice per cohort of these tissue-specific knockouts will be exposed to 10%, 21% and 50% $FiO_2$ starting 20 days of age. Overall survival and body weight will be monitored. Finally, cardiac echocardiograms (left ventricle) will be performed on these mouse models exposed to different oxygen tensions, at 35 days of age (Laboratory Animal Resource Center, University of California, San Francisco). This will allow the determining of contractility, any structural abnormalities and allow the monitoring of any arrhythmias. Sample sizes will be chosen to have 80% power to detect a 50% increase in overall survival based on representative data.

Female mice that are heterozygous for whole-body loss of PDHA1 will be tested. PDHA1 is located on the X chromosome. Therefore, male mice with a single loss-of-copy for PDHA1 have no remaining enzyme activity and do not survive to birth. Female mice that are heterozygous for this mutation are mosaics. Typically, ~40% of cells in their body are knockout for PDHA1 activity. While there are subtle defects in neurogenesis and neuronal number, the heterozygous mice survive into adulthood. Ten female mice with this genotype will be placed in 21% and 50% $FiO_2$ starting 30 days of age to determine if hyperoxia treatment unmasks the disease phenotype. Body weight and survival will be measured. This will allow the assessing of the hyperoxia-sensitivity of this more moderate model of disease.

Male mice harboring brain-specific knockouts of PDHA1 live up to 28 days after birth and exhibit abnormal neuronal excitability. Jakkamsetti, V. et al. (2019). Science translational medicine 11, no. 480 (2019): eaan0457. Ten male mice with this genotype will be placed in 10%, 21% and 50% $FiO_2$ starting 12 days of age. Overall survival and body weight will be monitored. Brain metabolism will be determined by conducting the enzyme activity assay of PDH, flux of glucose and pyruvate through PDH using isotopically labeled glucose or pyruvate, and steady-state metabolic profiles by an untargeted metabolomics in University of Utah metabolomics core in isolated brain tissues. Finally, neuropathology will be determined using neuroinflammation markers (e.g. GFAP) and neuronal death markers (e.g. NeuN). This will allow determining the therapeutic effects of hypoxia on the neuronal phenotypes of diseases caused by PDH deficiency.

Example 5: Body Weight of WKS Mouse Model in Normoxia Versus Hypoxia

Figure 3:
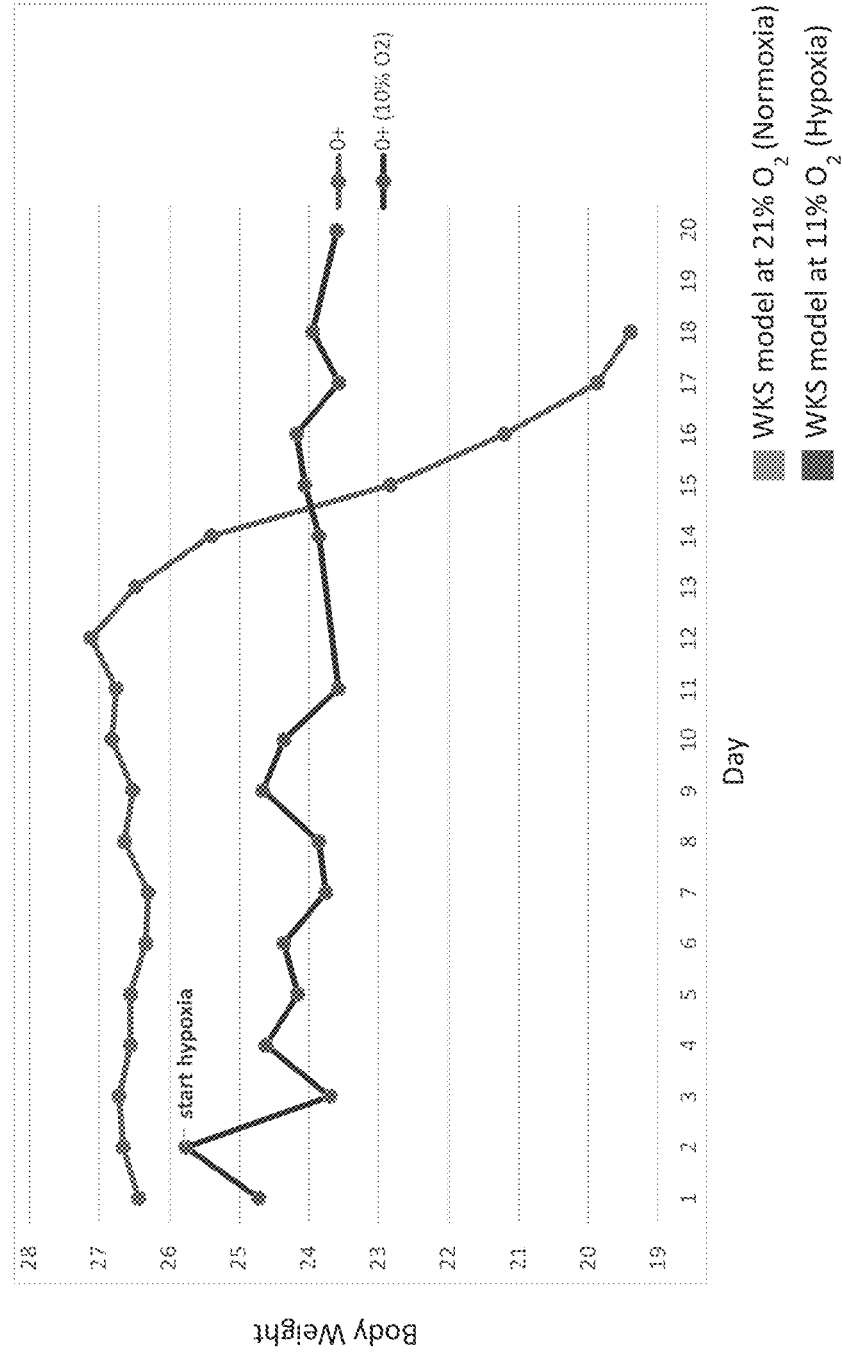
FIG. 3 depicts the body weight of Wernicke-Korsakoff (WKS) Animal Model (0 ppm thiamine and pyrithiamine injections) in normoxia versus hypoxia using the methods described herein.

FIG. 3 depicts the results of WKS mouse models being treated at 21% $O_2$ (normoxia) and 11% $O_2$ (hypoxia) for a span of 20 days. The body-weight of the WKS mouse models at 21% $O_2$ dropped significantly at Day 14, whereas the body-weight of the WKS mouse models at 11% $O_2$ did not. Over this time period, the WKS mouse models at 21% $O_2$ failed to exhibit physiological signs of WKS, indicating that hypoxia prevented disease onset. Hypoxia began on Day 3 of the experiment.

Figure 4:
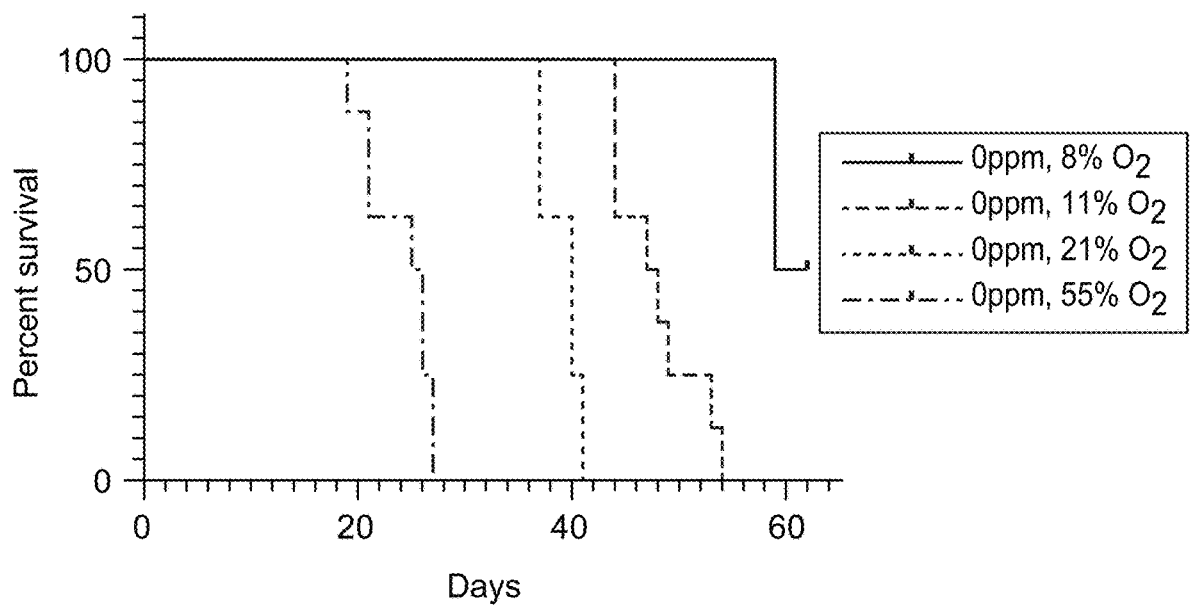
FIG. 4 depicts results of percentage survival (top) and body weight in grams (bottom) of mice on a thiamine-deficient diet kept in 55% $O_2$, 21% $O_2$, 11% $O_2$ or 8% $O_2$ environments.
Figure 4:
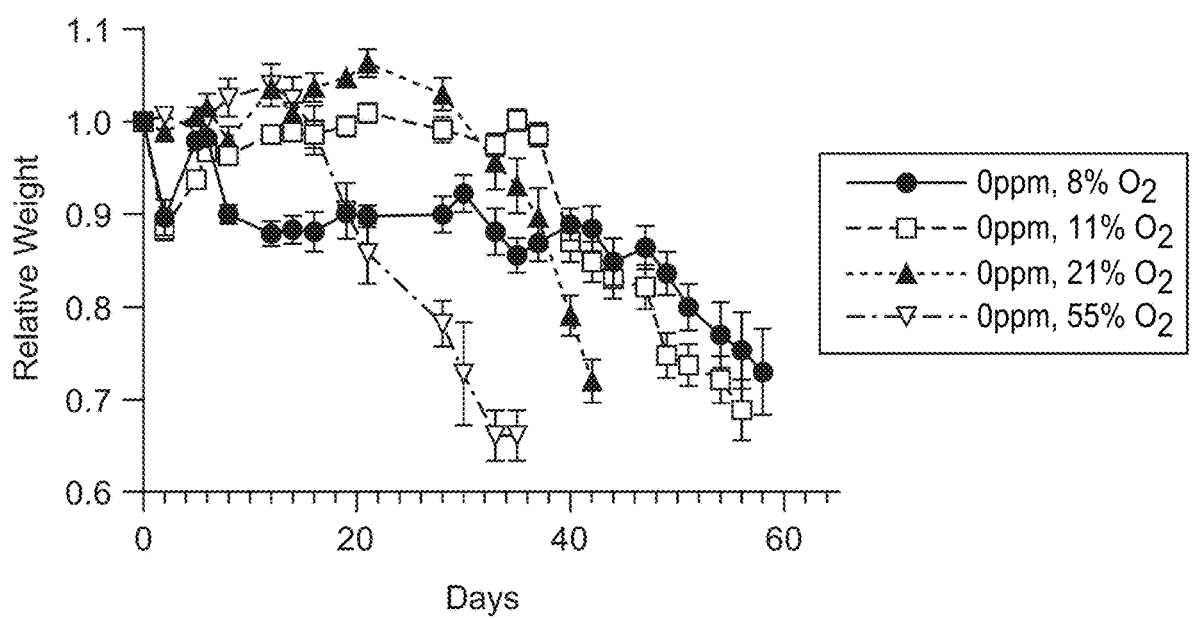

FIG. 4 depicts results of body weight and percentage survival of mice on a thiamine-deficient diet that were kept in 8% $O_2$, 11% $O_2$, 21% $O_2$ or 55% $O_2$ environments. Mice at 21% $O_2$ began to lose weight 21 days after being given a thiamine-deficient diet and had a median survival time of 37 days. Mice at 11% $O_2$ lost body weight at a slower rate and their survival time was extended by approximately 13 days. Extreme hypoxia of 8% $O_2$ further delayed the onset of weight loss and extended the survival time, and some mice were still alive at 60 days after being given a thiamine-deficient diet. On the other hand, 55% $O_2$ exacerbated the disease progression.

Example 6: Disease Progression of WKS Mouse Model in Low Versus High Oxygen

Figure 5:
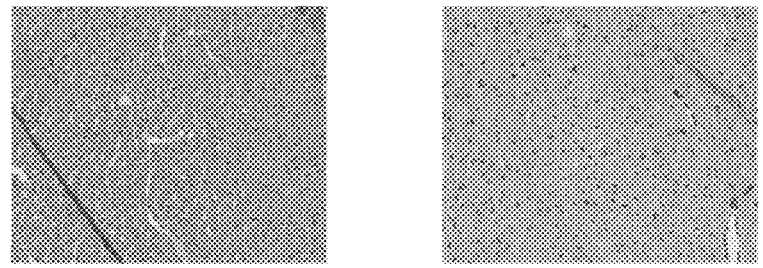
FIG. 5 depicts the neuropathology and cardio pathology of Wernicke-Korsakoff (WKS) Animal Model (0 ppm thiamine) in hyperoxia (55% oxygen).
Figure 5:
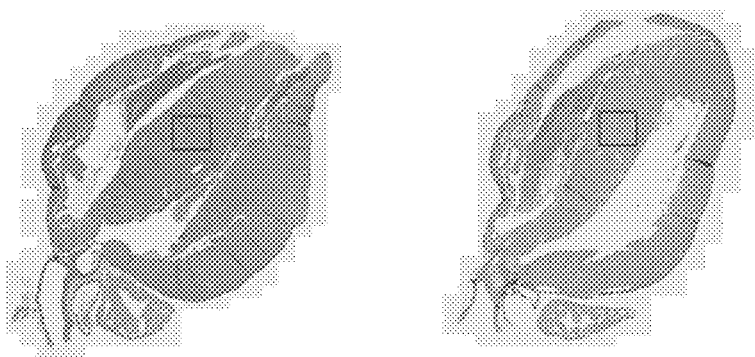
Figure 5:
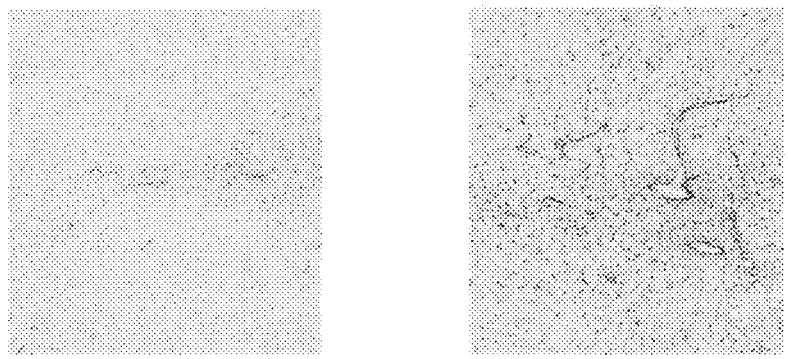
Figure 5:
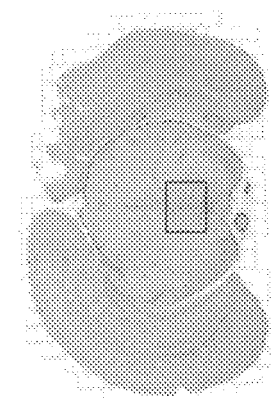

FIG. 5 depicts that thiamine deficiency causes neuroinflammation and dilated cardiomyopathy. Mice housed under 50% Fi $O_2$ were fed with the standard chow (containing 17 ppm thiamine, upper panel) or a thiamine-deficient diet (0 ppm thiamine, lower panel). In the severe disease state in accompany with 35% body weight loss, mice under a thiamine-deficient diet exhibit neuroinflammation in the brain stem regions (left, brown immunohistochemistry staining for GFAP, a neuroinflammation marker) and dilated cardiomyopathy (right, H&E staining).

Figures 6A, 6B, 6C, 6D, 6E:
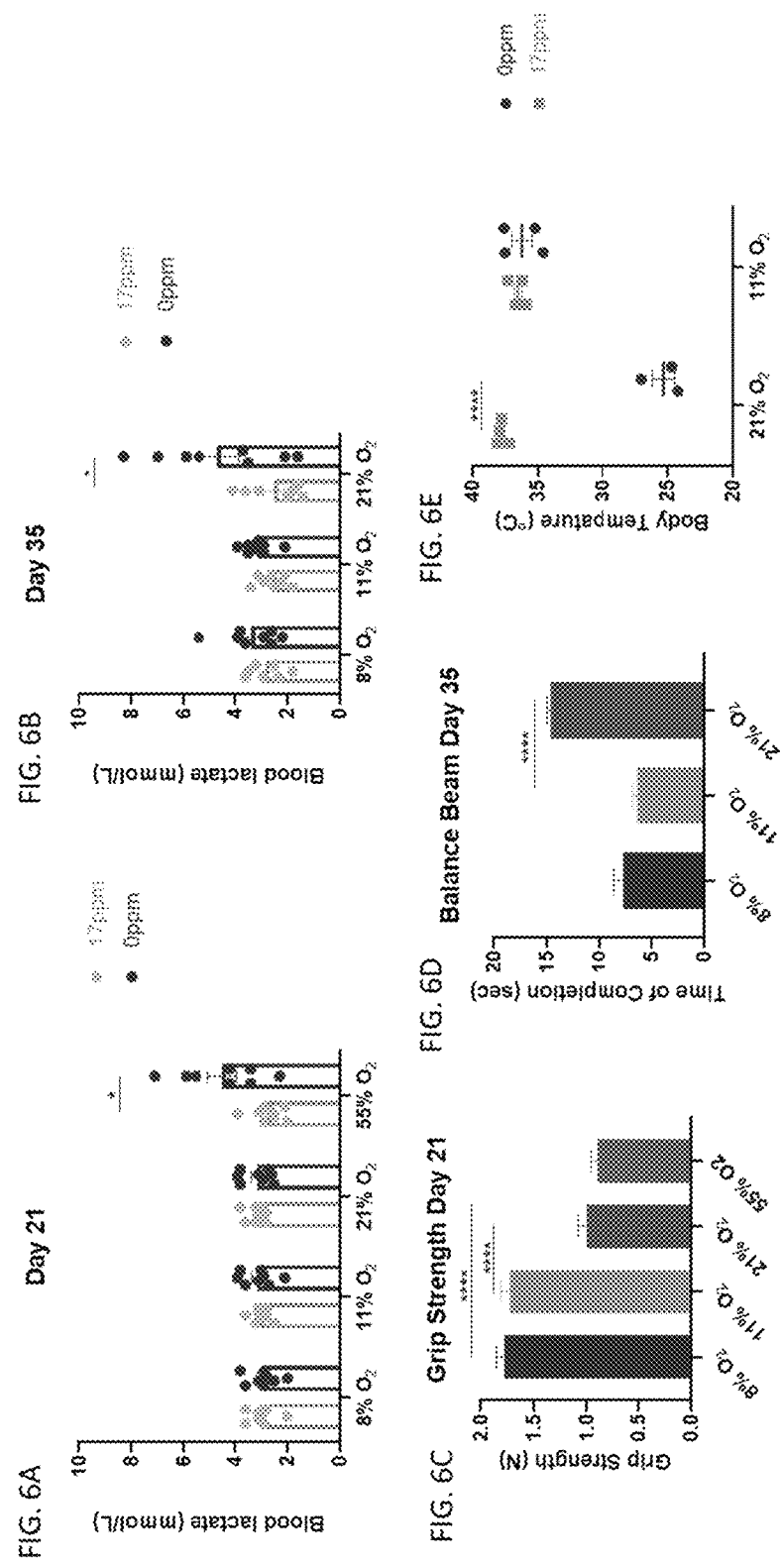
FIGS. 6A-6E depict results of hypoxia alleviating the symptoms caused by thiamine deficiency, including lactic acidosis at day 21 (FIG. 6A) and day 35 (FIG. 6B), muscle weakness (FIG. 6C), impaired balance and locomotion (FIG. 6D) and hypothermia (FIG. 6E) in the WKS Animal Model.

FIGS. 6A-6E depict the results of lowering $FiO_2$ on the symptoms caused by thiamine deficiency. Blood lactate measured in mice housed under different oxygen tensions 21 and 35 days after the diets started. The mice present lactic acidosis in the severe disease state under 55% and 21% oxygen at day 21 (FIG. 6A) and day 35 (FIG. 6B). Muscle strength assessed by grip strength of mice administered with 17 ppm or 0 ppm thiamine for 21 days. Muscle strength is compromised in mice with thiamine-deficiency under 55% and 21% oxygen (FIG. 6C). Mice administered with a thiamine-deficient diet for 43 days under normoxic air exhibit hypothermia, whereas mice kept under 11% $O_2$ had normal body temperatures (FIG. 6D). Mice administered with a thiamine-deficient diet for 43 days under normoxic air but not hypoxia exhibit hypothermia (FIG. 6E). Student's t-test * $p<0.05$,  $p<0.01$, ** $p<0.001$. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

[1] L. Chimeli, B. Harding, J. Lowe, H. V Vinters, S. Brandner, and W. Yong, *Neuropathology: A Reference Text of CNS Pathology*. 3rd Edition. 2013.

[2] K. O'Donnell, "Lactic Acidosis: A Lesser Known Side Effect of Thiamine Deficiency," *Pract. Gastroenterol.*, no. March, pp. 24-32, 2017.

[3] K. P. Patel, T. W. O'Brien, S. H. Subramony, J. Shuster, and P. W. Stacpoole, "The spectrum of pyruvate dehydrogenase complex deficiency: Clinical, biochemical and genetic features in 371 patients," *Mol. Genet. Metab.*, vol. 106, no. 3, pp. 385-394, 2012.

[4] C. L. Quinlan, R. L. S. Goncalves, M. Hey-Mogensen, N. Yadava, V. I. Bunik, and M. D. Brand, "The 2-oxoacid dehydrogenase complexes in mitochondria can produce superoxide/hydrogen peroxide at much higher rates than complex I," *J. Biol. Chem.*, vol. 289, no. 12, pp. 8312-8325, 2014.

[5] S. J. Yeaman, "The mammalian 2-oxoacid dehydrogenases: a complex family," *Trends Biochem. Sci.*, vol. 11, no. 7, pp. 293-296, 1986.

[6] I. Papandreou, R. a Cairns, L. Fontana, A. L. Lim, and N. C. Denko, "HIF-1 mediates adaptation to hypoxia by actively downregulating mitochondrial oxygen consumption.," *Cell Metab.*, vol. 3, no. 3, pp. 187-97, March 2006.

[7] J. Kim, I. Tchernyshyov, G. L. Semenza, and C. V Dang, "HIF-1-mediated expression of pyruvate dehydrogenase kinase: a metabolic switch required for cellular adaptation to hypoxia.," *Cell Metab.*, vol. 3, no. 3, pp. 177-85, March 2006.

[8] R. C. Sun and N. C. Denko, "Hypoxic regulation of glutamine metabolism through HIF1 and SIAH2 supports lipid synthesis that is necessary for tumor growth," *Cell Metab.*, vol. 19, no. 2, pp. 285-292, 2014.

[9] F. Paredes et al., "Poldip2 is an oxygen-sensitive protein that controls PDH and αKGDH lipoylation and activation to support metabolic adaptation in hypoxia and cancer," *Proc. Natl. Acad. Sci.*, vol. 115, no. 8, pp. 1789-1794, 2018.

[10] J. A. Mayr, R. G. Feichtinger, F. Tort, A. Ribes, and W. Sperl, "Lipoic acid biosynthesis defects," *J. Inherit. Metab. Dis.*, vol. 37, no. 4, pp. 553-563, 2014.

[11] N. J. Lake, M. J. Bird, P. Isohanni, and A. Paetau, "Leigh syndrome: neuropathology and pathogenesis.," *J. Neuropathol. Exp. Neurol.*, vol. 74, no. 6, pp. 482-92, 2015.

[12] A. Quaegebeur et al., "Deletion or inhibition of the oxygen sensor PHD1 protects against ischemic stroke via reprogramming of neuronal metabolism," *Cell Metab.*, vol. 23, no. 2, pp. 280-291, 2016.

[13] I. H. Jain et al., "Hypoxia as a therapy for mitochondrial disease.," *Science*, vol. 352, no. 6281, pp. 54-61, 2016.

[14] J. D. Arroyo et al., "A Genome-wide CRISPR Death Screen Identifies Genes Essential for Oxidative Phosphorylation," *Cell Metab.*, vol. 24, no. 6, pp. 875-885, 2016.

[15] A. S. Hazell, K. G. Todd, and R. F. Butterworth, "Mechanisms of neuronal cell death in Wernicke's encephalopathy," *Metab. Brain Dis.*, vol. 13, no. 2, pp. 97-122, 1998.

[16] J. Finsterer and S. Zarrouk-Mahjoub, "Biomarkers for Detecting Mitochondrial Disorders," *J. Clin. Med.*, vol. 7, no. 2, p. 16, 2018.

[17] S. B. Vafai and V. K. Mootha, "Mitochondrial disorders as windows into an ancient organelle," *Nature*, vol. 491, no. 7424, pp. 374-383, November 2012.

[18] A. Flynn, M. Macaluso, I. D'Empaire, and M. M. Troutman, "Wernicke's Encephalopathy: Increasing Clinician Awareness of This Serious, Enigmatic, Yet Treatable Disease," *Prim. Care Companion CNS Disord.*, vol. 17, no. 3, 2015.

[19] T. Taivassalo, A. Abbott, P. Wyrick, and R. G. Haller, "Venous oxygen levels during aerobic forearm exercise: An index of impaired oxidative metabolism in mitochondrial myopathy," *Ann. Neurol.*, vol. 51, no. 1, pp. 38-44, 2002.

[20] P. Jauhari, N. Sankhyan, S. Vyas, and P. Singhi, "Thiamine Responsive Pyruvate Dehydrogenase Complex Deficiency: A Potentially Treatable Cause of Leigh's Disease," *J. Pediatr. Neurosci.*, vol. 12, no. 3, pp. 265-267, 2017.

[21] C. G. Harper, M. Giles, and R. Finlay-Jones, "Clinical signs in the Wernicke-Korsakoff complex: A retrospective analysis of 131 cases diagnosed at necropsy," *J. Neurol. Neurosurg. Psychiatry*, vol. 49, no. 4, pp. 341-345, 1986.

[22] R. P. Vetreno, R. L. Ramos, S. Anzalone, and L. M. Savage, "Brain and behavioral pathology in an animal model of Wernicke's encephalopathy and Wernicke-Korsakoff syndrome," *Brain Res.*, vol. 1436, pp. 178-192, 2012.

[23] I. Watanabe, "Pyrithiamine-induced acute thiamine-deficient encephalopathy in the mouse," *Exp. Mol. Pathol.*, vol. 28, no. 3, pp. 381-394, 1978.

[24] P. J. Langlais, "Pathogenesis of Diencephalic Lesions in an Experimental Model of Wernicke's Encephalopathy," *Metab. Brain Dis.*, vol. 10, no. 1, 1995.

[25] S. Sidhu et al., "Tissue-specific pyruvate dehydrogenase complex deficiency causes cardiac hypertrophy and sudden death of weaned male mice," *Am. J. Physiol. Heart. Circ. Physiol.*, vol. 295, no. 3, pp. H946-H952, 2008.

[26] M. T. Johnson et al., "Inactivation of the murine pyruvate dehydrogenase (Pdha1) gene and its effect on early embryonic development," *Mol. Genet. Metab.*, vol. 74, no. 3, pp. 293-302, 2001.

[27] D. Lonsdale, "Thiamine and magnesium deficiencies: Keys to disease," *Med. Hypotheses*, vol. 84, no. 2, pp. 129-134, 2015.

[28] P. J. Brown et al., "Diet and Refsum's disease. The determination of phytanic acid and phytol in certain foods and the application of this knowledge to the choice of suitable convenience foods for patients with Refsum's disease," *J. Hum. Nutr. Diet.*, vol. 6, no. 4, pp. 295-305, 1993.

[29] A. Easter et al., "Thiamine Deficiency: A Case Presentation and Literature Review," pp. 1-6, 2014.

What is claimed is:

1. A method of alleviating a symptom of Wernicke-Korsakoff Syndrome, Wernicke encephalopathy, Korsakoff syndrome, Wet Beriberi, or Dry Beriberi in a subject, the method comprising:
    administering 5%-19% oxygen to the subject at a set interval for a set time period,
    wherein the symptom comprises reduced life expectancy and muscle weakness.

2. The method of claim 1, wherein the subject has Wernicke-Korsakoff Syndrome.

3. The method of claim 1, further comprising reducing a phenotypic characteristic of Wernicke-Korsakoff Syndrome, Wernicke encephalopathy, Korsakoff syndrome, Wet Beriberi, or Dry Beriberi, wherein the phenotypic characteristic is ophthalmoplegia, ataxia, confusion, vision change, loss of memory, hallucination, confabulation, or inability to form new memories.

4. The method of claim 1, further comprising administering an effective amount of thiamine.

5. The method of claim 4, further comprising reducing a phenotypic characteristic of Wernicke-Korsakoff Syndrome, Wernicke encephalopathy, Korsakoff syndrome, Wet Beriberi, or Dry Beriberi, wherein the phenotypic characteristic is ophthalmoplegia, ataxia, confusion, vision change, loss of memory, hallucination, confabulation, or inability to form new memories.

6. The method of claim 5, wherein the subject has Wernicke-Korsakoff Syndrome.

7. The method of claim 1, wherein a level of oxygen in the subject is measured by a pulse oximeter.

8. The method of claim 1, wherein the method comprises administering 5-10% oxygen.

9. The method of claim 1, wherein the method comprises administering 5-15% oxygen.

10. The method of claim 1, wherein the method comprises administering 5-18% oxygen.

11. The method of claim 1, wherein the method further comprises diagnosing the subject as having Wernicke-Korsakoff Syndrome, Wernicke encephalopathy, Korsakoff syndrome, Wet Beriberi, or Dry Beriberi.

12. The method of claim 1, wherein the set interval is once a day.

13. The method of claim 1, wherein the set interval is twice a day.

14. The method of claim 1, wherein the set interval is three times a day.

15. The method of claim 1, wherein the set time period is 1-10 days.

16. The method of claim 1, wherein the set time period is 5-15 days.

17. The method of claim 1, wherein the set time period is 10-20 days.

18. The method of claim 1, wherein the set time period is 15-25 days.

* * * * *